(12) United States Patent
Cibaud et al.

(10) Patent No.: US 10,841,125 B2
(45) Date of Patent: Nov. 17, 2020

(54) METHOD FOR TRANSMITTING DATA FROM A SENSOR

(71) Applicant: Orange, Paris (FR)

(72) Inventors: David Cibaud, Saint Egreve (FR); Marie-Jeanne Bouzid, Montbonnot-Saint-Martin (FR); Marc Berenguer, Revel (FR)

(73) Assignee: ORANGE, Paris (FR)

( * ) Notice: Subject to any disclaimer, the term of this patent is extended or adjusted under 35 U.S.C. 154(b) by 426 days.

(21) Appl. No.: 15/537,649

(22) PCT Filed: Dec. 17, 2015

(86) PCT No.: PCT/FR2015/053598
§ 371 (c)(1),
(2) Date: Jun. 19, 2017

(87) PCT Pub. No.: WO2016/097633
PCT Pub. Date: Jun. 23, 2016

(65) Prior Publication Data
US 2017/0359194 A1    Dec. 14, 2017

(30) Foreign Application Priority Data
Dec. 19, 2014  (FR) ..................................... 14 62866

(51) Int. Cl.
*H03M 7/30* (2006.01)
*G06F 17/18* (2006.01)
(Continued)

(52) U.S. Cl.
CPC .......... *H04L 12/2827* (2013.01); *G06F 11/30* (2013.01); *G06F 17/18* (2013.01);
(Continued)

(58) Field of Classification Search
CPC .. H04L 12/2827; H04L 12/2803; G06F 11/30; H04N 21/43615; H04N 21/44213
See application file for complete search history.

(56) References Cited

U.S. PATENT DOCUMENTS

2009/0204008 A1    8/2009  Beilin
2010/0298718 A1*  11/2010  Gilham ................. H04W 16/10
                                                      600/484
(Continued)

OTHER PUBLICATIONS

Sneha et al., "Enabling ubiquitous patient monitoring: Model, decision protocols, opportunities and challenges", Decision Support Systems 46 (2009) 606-619 (Year: 2009).*
(Continued)

*Primary Examiner* — Regis J Betsch
(74) *Attorney, Agent, or Firm* — David D. Brush; Westman, Champlin & Koehler, P.A.

(57) ABSTRACT

A method for transmitting data collected by at least one sensor to a monitoring device. The method includes, upon acquisition of a new piece of data by the at least one sensor, acts of calculating a deviation indicator indicating a deviation between the value of the new piece of data and a value predicted for this piece of data by a prediction model representative of previously acquired data, and transmitting the new piece of data to the monitoring device when the deviation indicator is higher than a threshold. Also provided are a monitoring method on a monitoring device, a terminal implementing the transmission method and a server implementing the monitoring method.

10 Claims, 7 Drawing Sheets

(51) Int. Cl.
  G16H 40/67    (2018.01)
  G06Q 10/04    (2012.01)
  G06F 11/30    (2006.01)
  H04L 12/28    (2006.01)
  H04L 12/64    (2006.01)
  H04L 29/06    (2006.01)
  G06Q 50/06    (2012.01)
  G06Q 10/06    (2012.01)
  H04N 21/436   (2011.01)
  H04N 21/442   (2011.01)
  G16H 50/30    (2018.01)

(52) U.S. Cl.
  CPC .......... *G06Q 10/04* (2013.01); *G06Q 10/06* (2013.01); *G06Q 50/06* (2013.01); *G16H 40/67* (2018.01); *H03M 7/30* (2013.01); *H03M 7/3079* (2013.01); *H03M 7/6011* (2013.01); *H04L 12/2803* (2013.01); *H04L 12/6418* (2013.01); *H04L 69/04* (2013.01); *H04N 21/43615* (2013.01); *H04N 21/44213* (2013.01); *G16H 50/30* (2018.01)

(56) References Cited

U.S. PATENT DOCUMENTS

| | | | | |
|---|---|---|---|---|
| 2011/0213225 A1* | 9/2011 | Bernstein | ............ | A61B 5/1486 600/309 |
| 2014/0032153 A1* | 1/2014 | Mayer | ................ | G01N 33/0006 702/104 |
| 2015/0199010 A1* | 7/2015 | Coleman | .............. | A61B 5/0006 345/156 |
| 2015/0331418 A1* | 11/2015 | Nogueira | ............ | A61M 5/1723 702/104 |
| 2017/0024539 A1* | 1/2017 | Webb | .................... | A61B 5/002 |

OTHER PUBLICATIONS

Kafeza et al., "Alerts in Mobile Healthcare Applications: Requirements and Pilot Study", IEEE Transactions on Information Technology in Biomedicine, vol. 8, No. 2, Jun. 2004 (Year: 2004).*

English Translation of the Written Opinion of the International Searching Authority dated Mar. 14, 2016 for corresponding International Application No. PCT/FR2015/053598, filed Dec. 17, 2015.

International Search Report dated Mar. 14, 2016 for corresponding International Application No. PCT/FR2015/053598, filed Dec. 17, 2015.

Rajasekaran M Pallikonda et al., "Elderly patient monitoring system using a wireless sensor network", Telemedicine and E-Health,, vol. 15, No. 1, 2009, pp. 73-79, XP002579874.

Jie Yin et al., "Sensor-Based Abnormal Human-Activity Detection", IEEE Transactions on Knowledge and Data Engineering, IEEE Service Center, Los Alamitos, CA, US, vol. 20, No. 8, Aug. 2008 (Aug. 2008), pp. 1082-1090, XP011224113.

Noury et al., "Monitoring Behavior Home Using a Smart Fall Sensor and Position Sensors", 1st Annual International IEEE-EMBS Special Topic Conference on Microtechnologies in Medicine and Biology, Proceedings (CAT.NO.OOEX451) IEEE Piscataway, NJ, USA, Piscataway, NJ : IEEE Operations Center, 2000, US, Oct. 12, 2000 (Oct. 12, 2000), pp. 607-610, XP007908797.

Alemdar H et al., "Wireless sensor networks for healthcare: A survey" Computer Networks, Elsevier Science Publishers B.V., Amsterdam, NL, vol. 54, No. 15, Oct. 28, 2010 (Oct. 28, 2010), pp. 2688-2710, XP027289934.

Witten Opinion of the International Searching Authority dated Mar. 14, 2016 for corresponding International Application No. PCT/FR2015/053598, filed Dec. 17, 2015.

* cited by examiner

METHOD FOR TRANSMITTING DATA FROM A SENSOR

CROSS-REFERENCE TO RELATED APPLICATIONS

This Application is a Section 371 National Stage Application of International Application No. PCT/FR2015/053598, filed Dec. 17, 2015, which is incorporated by reference in its entirety and published as WO 2016/097633 A1 on Jun. 23, 2016, not in English. cl TECHNICAL FIELD The invention relates to the field of home automation and relates in particular to the collection and the monitoring of data from sensors of an environment.

PRIOR ART

Many systems, such as home automation systems, use sensors distributed in an environment. These sensors are used by such systems to measure different values, such as, for example, a temperature or the activity of a person for example. Sensors can also be used to detect a presence, the opening or the closing of a door or even the state of a motorized device. Some kinds of sensors can also be worn by a user or a domestic animal. There are for example connected bracelets or watches suitable for being recognized by the home automation system and for transmitting information on the movements of the wearer thereof.

The data captured by such sensors are generally transmitted to a server capable, for example, of controlling actions in response to certain events detected, of raising alerts or of formatting certain data for presentation to a user. The transmission of the data between the sensor and the server is generally performed via a wireless network such as, for example, a wireless network of 3G, Wifi or Bluetooth type.

Some sensors perform measurements continuously and track the trend of their environment. Such is the case for example for sensors such as temperature, light, wind speed or even acceleration sensors. This continuous operation generates a continuous stream of data which sometimes requires a significant bandwidth. In particular, some acceleration sensors embedded in objects such as smartphones, bracelets or connected watches measure the accelerations on three axes at high frequencies, thus generating a significant stream of data which requires a significant bandwidth regularly causing network congestions. When the data captured cannot be processed by the sensor itself and have to be transmitted to other equipment, congestions can occur on the network.

In order to avoid exhausting the energy resources of the sensor too quickly, the sensor is often provided with a memory in which the captured data are stored, the content of the memory being transmitted regularly to the server. Thus, the network interface is invoked only intermittently and the sensor can limit the energy consumption linked to the transmission of the data. However, this approach requires the sensor to be equipped with a quantity of memory suited to the data acquisition frequency, which is not always economically viable.

Thus, there is a clear need for a solution that is less intensive in terms of network capacity or memory capacity for the collection and the monitoring, by a server, of data transmitted continuously by a sensor.

SUMMARY OF THE INVENTION

To this end, the invention proposes a method for transmitting, to a monitoring device, data collected by at least one sensor such that it comprises, on acquisition of a new datum by the at least one sensor, the following steps:
  computation of an indicator of deviation between the value of the new datum and a value predicted for this datum by a prediction model representative of data previously acquired, and
  transmission of the new datum to the monitoring device when the deviation indicator is above a threshold.

When the sensor obtains a new datum, for example when it obtains a temperature measurement by means of a thermal probe with which it is associated, the value of this datum is compared to the value predicted by a prediction model. The prediction model is determined from data measured over a preceding period. It can for example concern an affine law, a linear regression or even, for example, a polynomial regression. Such a deviation indicator is computed from the measurement and from the value of this measurement predicted by the model so as to validate or invalidate the fit of the measured value with the model. The deviation indicator can for example be a difference between the measured value and the predicted value, or even a value deriving from a statistical study taking into account several measurements, such as, for example, a test of $\chi^2$ (Khi-2) which makes it possible to validate the fit of a series of data with a model. When the measured value fits with the value predicted by the model, it is not transmitted. In this way, only the data which do not correspond to the predictions are transmitted. The method thus makes it possible to considerably reduce the number of measurements to be transmitted when the measured values fit with a prediction model.

For example, when a prediction model models the trend of temperature over a period of 24 hours, a sensor implementing the method may compare temperature readings with this model and transmit only the readings which do not fit with the model. The sensor thus limits the use of the network and increases its autonomy. Since the values that fit the model are disregarded, the method does not require significant storage space.

According to a particular embodiment, the method is such that it comprises the following prior steps:
  transmission to the monitoring device of the data acquired by the at least one sensor over a predetermined time period, and
  reception, from the monitoring device, of a prediction model representative of data transmitted.

The data measured over a period are transmitted to a monitoring device, such as, for example, a server that has processing capacities. In return, the device implementing the method receives a prediction model representative of the data transmitted. Consider for example a connected sensor implementing the transmission method. The sensor measures temperatures over a period of 24 hours and transmits the corresponding readings for the period to a server. In return, the sensor receives a prediction model representative of the data measured over the period. In this way, the sensor has a prediction model based on an observation of the measurements over a preceding period enabling it to effectively select the data to be transmitted. Since the determination of the prediction model is performed by other equipment, the sensor does not require significant processing capacities.

The invention relates also to a method for monitoring by a monitoring server using data from at least one sensor, characterized in that it takes into account, to replace a sensor value not received, a value predicted by a prediction model representative of data previously received as long as a new datum, for which an indicator of deviation between its value and the value predicted for this datum is above a threshold, is not received.

The monitoring server can thus analyze, store and/or make available to other equipment all the values acquired by one or more sensors, including the data which have not been received over an observation period. For that, the server uses a prediction model representative of data received previously and that make it possible to obtain a predicted value for the measurements which have not been received. In this way, the data which fit with the corresponding values predicted by the model do not have to be transmitted to the monitoring server because they can be obtained by the server from the model. The method thus makes it possible to significantly limit the quantity of data exchanged between a sensor and a monitoring server.

According to a particular embodiment, the monitoring method is such that it also comprises the following steps:
reception of data from the at least one sensor over a predetermined time period,
computation of a predictive model representative of the data received over the period, and
transmission of the predictive model to the at least one sensor.

A monitoring device which implements such a monitoring method receives data from a measurement apparatus, from a detector or for example from a sensor such as a motion, temperature, wind or even light sensor, the data received corresponding to a determined time period. This can be a period of an hour, of a day, of a week or of a month for example. At the end of the period concerned, the monitoring device determines a predictive model representative of the trend of the measurements over the period. For example, the monitoring device can model the data by an affine law, a linear or polynomial regression, a normal law or any other statistical tool suitable for modeling a series of data. The monitoring device then transmits the characteristics of the model to the sensor. The model can be representative of data from several sensors.

In this way, the sensor does not need to have a significant processing capacity because the determination of the model is undertaken by the monitoring device. Also, the device can retain a copy of the model in order to reconstruct a full set of measurements in subsequent periods from, on the one hand, data transmitted by the sensor which do not fit with the model and, on the other hand, the copy of the model that it retains.

According to a particular embodiment, the monitoring method is such that it also comprises, on reception of a new datum from the at least one sensor, a step of updating of the predictive model.

The monitoring method makes it possible to take into account received data to update the prediction model. Thus, the prediction model can be adapted when the readings transmitted by the sensors change. In this way, one item of equipment can interrogate the prediction model of the server to learn the value of the different measurements performed by the sensor, whether or not they have been transmitted thereby. Also, since the model is representative of the data measured over the period, it is not necessary to retain the data used for the creation thereof. Thus, only the prediction model is retained and the storage space needed to store data is very limited.

According to a particular embodiment, the method is such that it comprises a step of transmission of the updated model to the at least one sensor.

The model is updated from data which do not fit with the model available to the sensor, otherwise they would not have been transmitted. When the model is updated, a server implementing the monitoring method can transmit this new model to the corresponding sensor so as to reduce the number of measurements to be transmitted for subsequent periods.

According to a particular embodiment, the method is such that the updating step is performed when the frequency of reception of new data is above a threshold.

The frequency of the data received increases when the data measured by a sensor implementing the transmission method no longer fit with the model. The method thus makes it possible to update the model and to transmit it to the sensor when it no longer fits with the measured data.

An updated version of the prediction model can also be transmitted to the sensor when data are received at regular intervals recurrently from one period to another. For example, if a measurement period of 24 h is being considered and the data are being received daily always at a certain time, the method may detect an absence of fit with the model and transmit a new updated version to the sensor.

The invention relates also to a device for transmitting, to a monitoring device, data collected by at least one sensor such that it comprises the following modules:
an acquisition module for a datum measured by the at least one sensor,
a computer suitable for computing an indicator of deviation between the value of the new datum and a value predicted for this datum by a prediction model representative of the data previously acquired,
a comparator suitable for comparing the deviation indicator to a threshold, and
a communication model suitable for transmitting a new datum to the monitoring device when the deviation indicator is above the threshold.

According to a particular embodiment, the transmission device is such that the communication module is also suitable for receiving a prediction model representative of the data transmitted from the monitoring device.

According to another aspect, the invention relates to a monitoring device based on data from at least one sensor and such that it comprises:
a communication module suitable for receiving data from at least one sensor of a monitoring system,
a module for reading a value predicted by a prediction model representative of sensor data previously received,
a monitoring module suitable for taking into account, to replace a sensor value not received, the predicted value as long as a new datum, for which an indicator of deviation between its value and the value predicted for this datum is above a threshold, is not received by the communication module.

According to a particular embodiment, the monitoring device is such that it also comprises a computer suitable for computing a predictive model representative of data received over a predetermined period, and that the communication module is also suitable for transmitting the predictive model to at least one transmission device.

The invention relates also to a terminal comprising a transmission device as described above.

The invention relates also to a server comprising a monitoring device as described above.

The invention relates also to a computer program comprising instructions for executing the transmission method and/or the monitoring method, when the program is run by a processor.

The invention relates also to a processor-readable information medium on which is stored a computer program comprising instructions for executing steps of the transmission method and/or of the monitoring method.

The different embodiments or features mentioned above can be added independently or in combination with one another, to the steps of the transmission method or of the monitoring method.

The servers, terminals, devices, programs and information media offer at least advantages similar to those provided by the corresponding methods described above.

LIST OF FIGURES

Other features and advantages of the invention will become more clearly apparent on reading the following description of a particular embodiment, given as a simple illustrative and nonlimiting example, and the attached drawings, in which.

DETAILED DESCRIPTION

Figure 1:
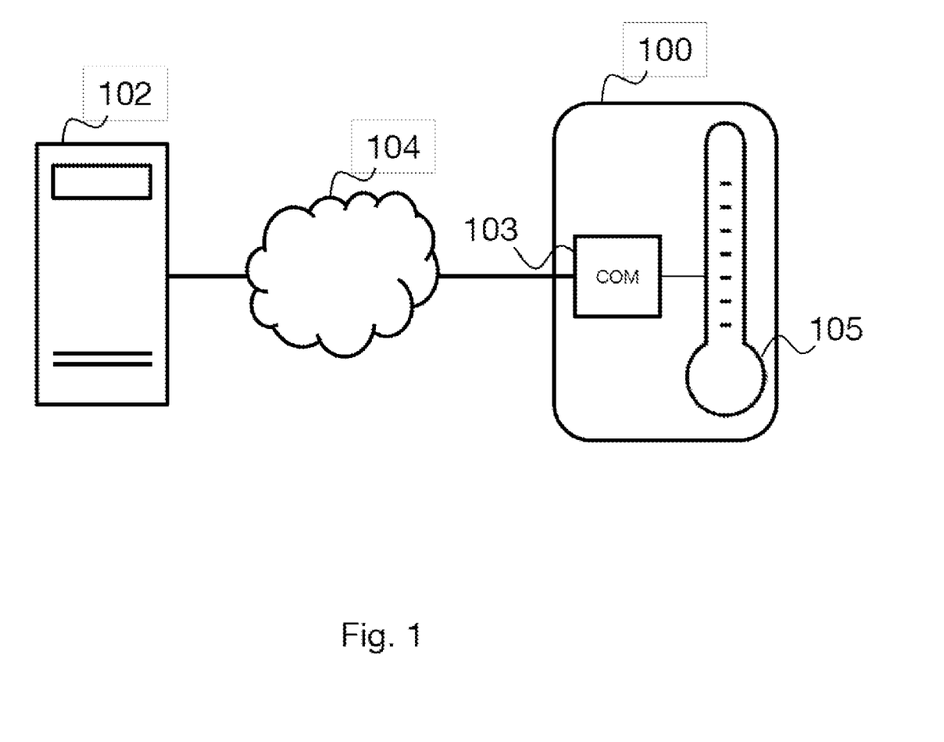
FIG. 1 shows a simplified illustration of an architecture suitable for implementing the transmission and monitoring methods according to a particular embodiment of the invention.

FIG. 1 shows a simplified illustration of the architecture of a monitoring system suitable for implementing the transmission and supervision methods according to a particular embodiment of the invention. It represents in particular a transmission device 100 comprising a thermal sensor 105 and a network interface 103 suitable for transmitting, for example, temperature readings measured by the sensor 105 to a server 102 via a network 104. The transmission device can, in another exemplary embodiment, comprise several measurement sensors of different types. This transmission device can for example be a communication terminal of "smartphone" type in which sensors are incorporated. It can also be a simple temperature transmission device as illustrated in FIG. 1. The network interface 103 is also capable of receiving data transmitted by the server 102, such as, for example, predictive models computed by the server 102 from data transmitted by the sensor 105. The server 102 can be hosted, for example, on a domestic gateway of a local area network and communicate with the transmission device 100 via a local area network. Various network technologies can be used, such as, for example, a Wifi, Ethernet or even Bluetooth network. It can also be hosted in a communication network of Internet type and communicate with the transmission device 100 via an Internet or 3G network for example. Although the invention is described here using the example of a temperature sensor, it is applicable to different types of sensors and is particularly advantageously applicable with sensors with a high measurement frequency, such as, for example, accelerometers or gyroscopes. The monitoring system represented here comprises only a single transmission device comprising a single sensor 105 but, according to other examples, the transmission device can comprise a plurality of sensors and the monitoring system can comprise a plurality of transmission devices 100.

Figure 2:
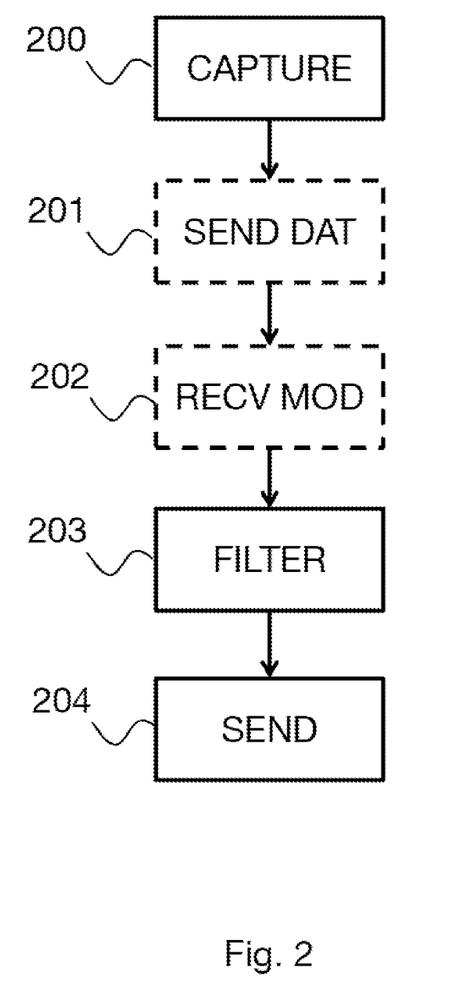
FIG. 2 illustrates the main steps of the transmission method according to a particular embodiment of the invention.

FIG. 2 illustrates the main steps of the transmission method according to a particular embodiment of the invention.

In a step 200, the transmission device 100 obtains data measured by the temperature sensor 105. In other embodiments, the data can originate, for example and in a non-exhaustive manner, from sensors suitable for measuring accelerations, angular speeds or even magnetic fields. The data can also be obtained from several sensors or from several instances of a same type of sensor. For example, the data can originate from an accelerometer suitable for measuring accelerations on 3 axes.

In a step 203, the data obtained from the thermal sensor 105 are compared to a predictive model stored for example in a memory of the device. The model can also be stored in a database of the network 104 and can be consulted by the device or of the sensors.

Figure 4A:
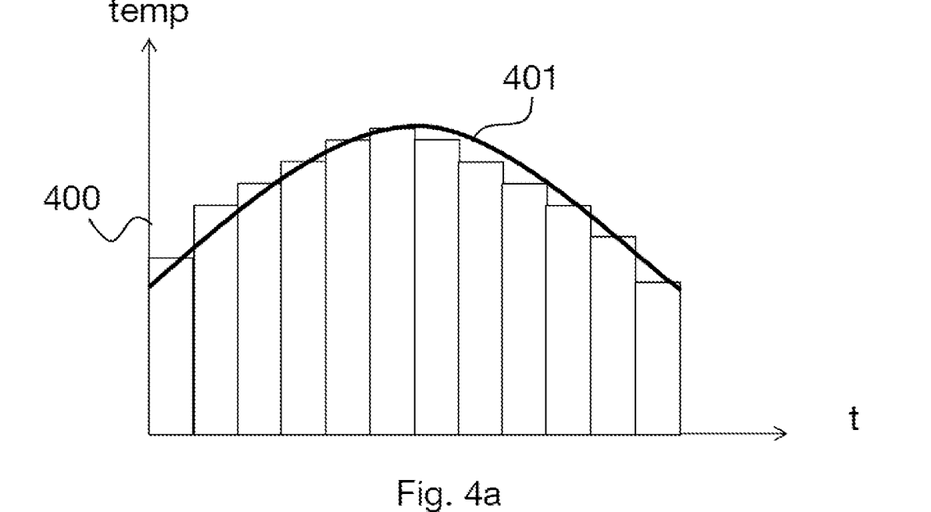
FIGS. 4a and 4b represent two series of measurements acquired by a sensor over a time period on which are overlaid two curves illustrating a predictive model for said periods.

The predictive model used is representative of the trend of the data measured by the sensor. This model can for example be a numeric function of affine type which, for a given instant, makes it possible to predict the value of a measurement. According to other embodiments, the data are modeled for example by a linear or polynomial regression or any other mathematical or statistical function suitable for describing the trend of the series of data measured. FIG. 4a represents, for example, a vertical line chart illustrating 12 temperature readings 400 over a period of 24 hours, at the rate of one measurement every two hours. In this example, the data are modeled by a normal law whose mean and variance are determined, for example, by successive tests. This representative model of the data is represented on the figure by the curve 401.

A deviation indicator is computed from a datum obtained from the sensor 105 and from its predictive value according to the predictive model so as to validate or invalidate the fit of the measured value with the value predicted by the model. The fit can be verified for example by measuring the deviation between the measured value and the predicted value, or, according to a particular embodiment, from a value obtained from a statistical study taking into account several measurements, or even for example from a test of $\chi^2$ (Khi-2) making it possible to validate the fit of a series of data with a model.

In the step 204, the data which do not fit with the model are transmitted to the server 102 via the network. The data which do fit with the model are, for their part, disregarded, so as to reduce the quantity of data transmitted over the network.

Figure 4B:
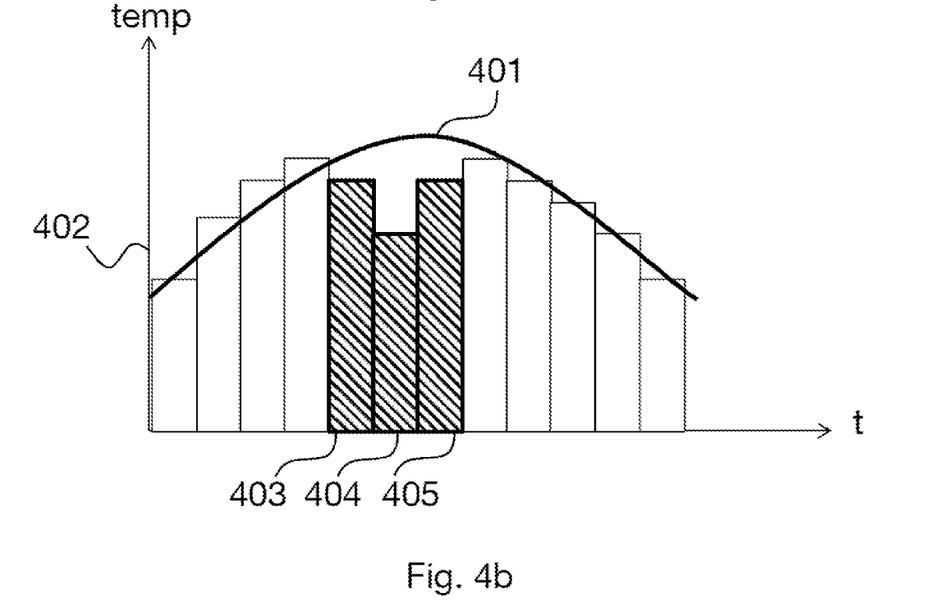

FIG. 4b represents a vertical line chart illustrating 12 temperature readings 402 over a period of 24 hours, at the rate of one measurement every two hours. In this example, the data are modeled by the same normal law as that represented in FIG. 4a, represented by the curve 401. In this example, the readings 403, 404 and 405 no longer correspond to the predictive model and the comparison of the deviation indicator with a predetermined tolerance threshold designates these readings as having to be transmitted to the server. Thus, only the readings 403, 404 and 405 are transmitted over the period.

According to a particular embodiment, the transmission method comprises an initialization phase during which no predictive model is available for the transmission device 100. During the step 201, all the measurements obtained during an initialization period are transmitted to the server 102 because, if there is no predictive model available, it is not possible to compute a deviation indicator. At the end of this first period, the server 102 transmits a predictive model computed from the data transmitted by the transmission device 100 during the initialization period. Thus, a predictive model representative of the data measured over the initialization period is received in the step 202. This model can then be used to verify the fit of the data from the sensor 100 in subsequent periods.

Figure 3A:
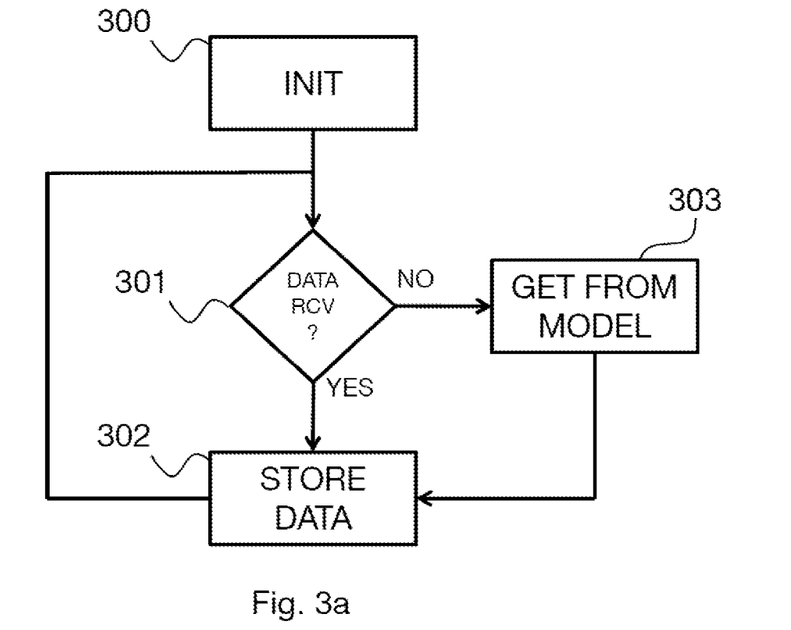
FIGS. 3a and 3b illustrate the main steps of the monitoring method according to a particular embodiment of the invention.

FIG. 3a represents steps that can be performed to implement the monitoring method according to a particular embodiment of the invention. The method is for example implemented on the server 102 described with reference to FIG. 1.

In the step 300, the server 102 initializes a monitoring task for the data obtained from the transmission device 100 with the aim, for example, of storing, in a database, the temperatures read by the temperature sensor 105 during the day.

For each time band, the server verifies, in the step 301, whether a datum from the transmission device has been received. For that, the server stores, for example in a random access memory, the data received and the time band to which they correspond. If a datum is found in the memory for a time band, this datum stored in the database in the step 302 and the next time band can be processed.

When, in the step 301, a datum is not found in the random access memory for a given time band, the server 102 assesses, in the step 303, a predictive model representative of data previously measured by the sensor. The assessment of this model allows the server 102 to obtain a predictive value for the time band concerned when a datum is not received.

Figure 3B:
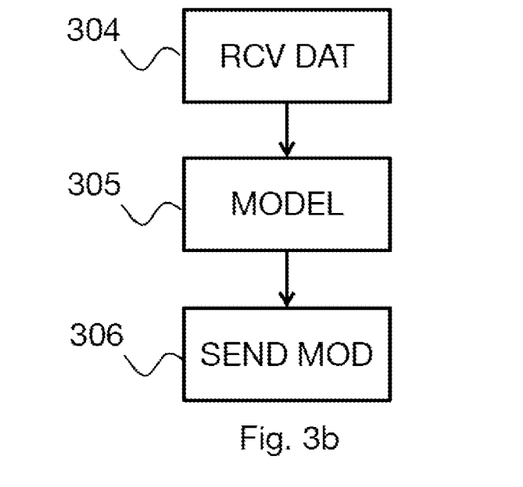

FIG. 3b illustrates steps of the monitoring method according to a particular embodiment of the invention.

In an initial step 304, the server 102 receives measurements relating to a given period from the transmission device 100. These data are for example transmitted by the transmission device 100 in the initialization step 201 described with reference to FIG. 2 and corresponding to the readings performed by the sensor over a first initialization period. According to a particular embodiment, these data are stored by the server in a database or a random access memory.

From these data, the server 102 computes, in the step 305, a predictive model representative of the data received over the period concerned. For that, the server can determine parameters of a numeric function, such as, for example, parameters of a function based on an affine or normal law or even a polynomial function. The number and the value of the parameters are chosen so as to obtain a function for which the values approximate measurements transmitted by the transmission device. The choice of the parameters can be made according to different optimization techniques known to those skilled in the art, such as, for example, a least squares optimization method or a splines-type technique.

According to another particular embodiment, the data to be modeled are segmented into a plurality of time bands, each of the bands being modeled independently by a numeric function and parameters, said parameters being determined for example by an optimization method of least squares or splines type.

In the step 306, the model is transmitted to the transmission device 100, for example in the form of a numeric function and parameters computed in the preceding step.

In this way, the monitoring method relieves the transmission device of the step of computation of the model which is particularly costly in terms of computation time.

At the end of the step 306, a copy of the predictive model is retained on the server 102 such that, subsequently, according to the steps described with reference to FIG. 3a, if an item of equipment interrogates the server to consult a measurement transmitted by the sensor, or for the requirements of a monitoring task, the server can assess the predictive model to learn the value of a measurement which has not been received. Thus, according to a particular embodiment, there is no need to retain the data from which the model was computed and the data received in the step 304 can be deleted in order not to unnecessarily occupy storage space on the server.

According to a particular embodiment, the data set initially used to compute the model is stored in a database. On reception of a new datum from the transmission device, the corresponding datum is replaced by the new datum in the database. The server uses this modified data set to compute a new predictive model. For that, the server once again executes the step 305 from the modified data set stored in the database.

According to a particular embodiment, when the model is updated by the server 102 following the reception of a new datum, this updated model is transmitted to the transmission device 100. The method thus makes it possible to improve the fit of the data from the sensor 105 with the predictive model so as to further reduce the quantity of the data exchanged between the transmission device 100 and the server 102.

According to a particular embodiment, the server 102 measures the frequency at which measurements are transmitted by the transmission device 100. For that, the server computes, for example, an indicator that takes into account the frequency of reception of the measurements over a period and the number of measurements transmitted initially by the transmission device 100 in the step 304. Since the measurements are transmitted only when they do not fit with the model, the more measurements the server receives, the less the model fits with the measured data. Thus, when the indicator is above a predetermined threshold, the server recomputes a predictive model on the basis of the latest data received for the period and transmits this new model to the transmission device.

According to a particular embodiment, the server 102 analyzes the temporal distribution of the received data. When, for example, received data are grouped together over a restricted time interval relative to the observation period, only the part of the model corresponding to this time interval is updated from the new data and transmitted to the transmission device. For example, when the temperature transmission device 100 uses a 24-hour predictive model to filter the sending of the temperature readings and the server 102 receives readings corresponding to the time interval [1200 hours-1400 hours], the server can deduce therefrom that the model used by the sensor is no longer suitable for this time period. The server 102 then computes a new predictive model representative of the data received over the interval [1200 hours-1400 hours] and transmits this new model to the transmission device 100. The method thus makes it possible to update the predictive model without the need to recompute it in its entirety. This embodiment thus preserves the computation resources of the server and the bandwidth for transmitting the model.

Figure 7:
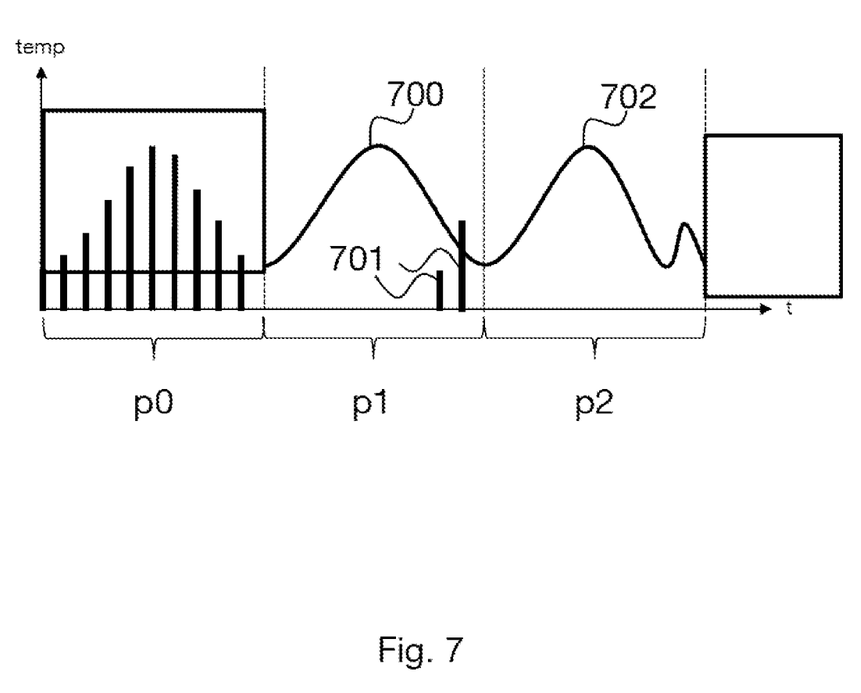
FIG. 7 is a diagram illustrating the implementation of the transmission method over 3 consecutive periods.

FIG. 7 gives a summary illustration in the form of a diagram of the temperature readings transferred between the transmission device 100 and the server 102. The figure shows three periods of operation P0, P1 and P2, each period having for example a duration of 24 hours. The period P0 is an initialization period. During this period, the transmission device 100 does not have a predictive model and all the measurements are transmitted to the server 102. At the end of the period P0, the server 102 computes and transmits to the transmission device a predictive model according to the steps 301 and 302 described previously. In the period P1, the transmission device implements a filtering of the measurements from the predictive model 700 by verifying the fit of the measurements with the model according to the step 203. Only the measurements which do not fit with the model, such as the measurements 701 for example, are transmitted to the server. At the end of the period P1, the server analyzes the distribution of the measurements received and decides to update the predictive model from these new measurements and to transmit it to the transmission device 100 so as to reduce the traffic. In the period P2, the updated model 702 is used by the transmission device 100 to filter the measurements. Since the model fits with the measured data, no measurement is transferred.

Figure 5:
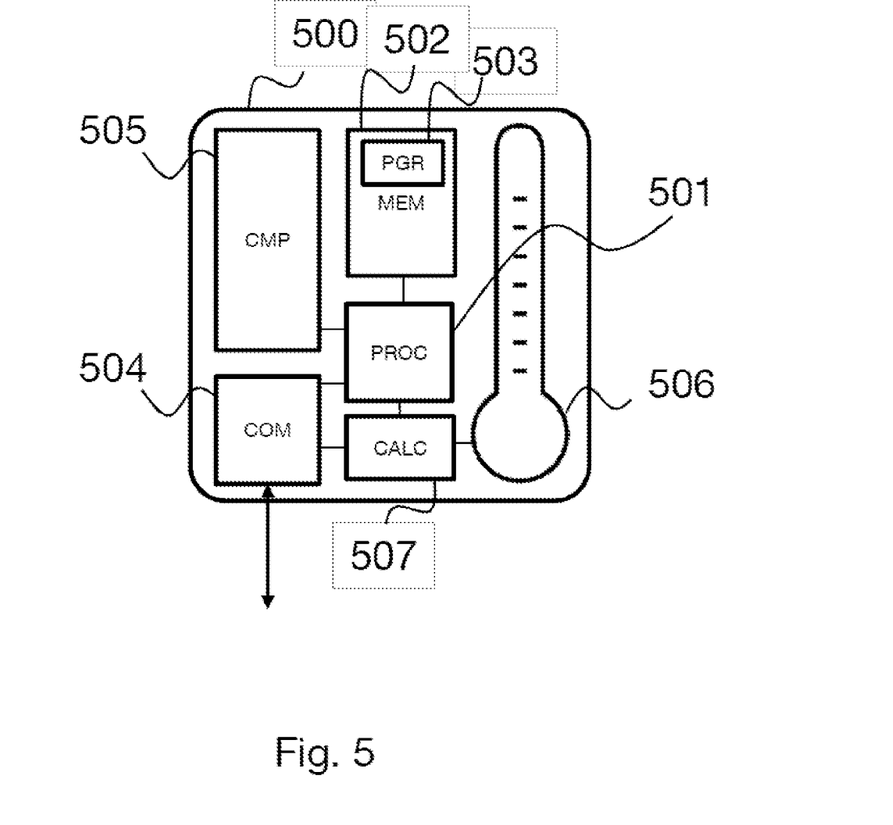
FIG. 5 illustrates a simplified architecture of a transmission device according to a particular embodiment of the invention.

FIG. 5 illustrates a device 500 implementing the transmission method according to a particular embodiment of the invention. The device comprises a storage space 502, for example a memory MEM, a processing unit 501 equipped for example with a processor PROC. The processing unit can be driven by a program 503, for example a computer program PGR, implementing the transmission method as described in the invention with reference to FIG. 2, and notably the steps of computation of an indicator of deviation between the value of the new datum and a value predicted for this datum by a prediction model representative of data previously acquired, and of transmission of the new datum to the monitoring device when the deviation indicator is above a threshold. According to a particular embodiment, the device also implements the steps of transmission to the monitoring device of the data acquired by the at least one sensor over a predetermined time period, and of reception, from the monitoring device, of a prediction model representative of the transmitted data.

On initialization, the instructions of the computer program 503 are for example loaded into a RAM memory (Random Access Memory in English) before being executed by the processor of the processing unit 501. The processor of the processing unit 501 implements the steps of the transmission method according to the instructions of the computer program 503.

For that, the device comprises, in addition to the memory 502, communication means 504 (COM) enabling the device to connect to a telecommunication network and to exchange data with other devices via the telecommunication network, and in particular to transmit measurements to a server and to receive a predictive model. According to a particular embodiment, the device further comprises a module for acquiring a measurement 506 suitable for capturing, for example, a physical quantity linked to the environment or to movements. For example, the acquisition module 506 is a temperature sensor, an accelerometer, a gyroscope, a compass, an anemometer or even an interfacing module suitable for connecting a remote sensor. This interfacing unit may correspond for example to a USB (Universal Serial Bus), Bluetooth, Ethernet interface or even, for example, to a communication bus. The device also comprises a computer 507 (CALC) suitable for computing an indicator of deviation between the value of the new datum and a value predicted for this datum by a prediction model representative of the data previously acquired by the acquisition module 506, a comparator 505 (CMP) suitable for comparing the deviation indicator to a tolerance threshold and allowing the communication module 504 to transmit a new datum to the monitoring device when the deviation indicator is above the threshold.

According to a particular embodiment, the device can be incorporated in a terminal or a home gateway.

Figure 6:
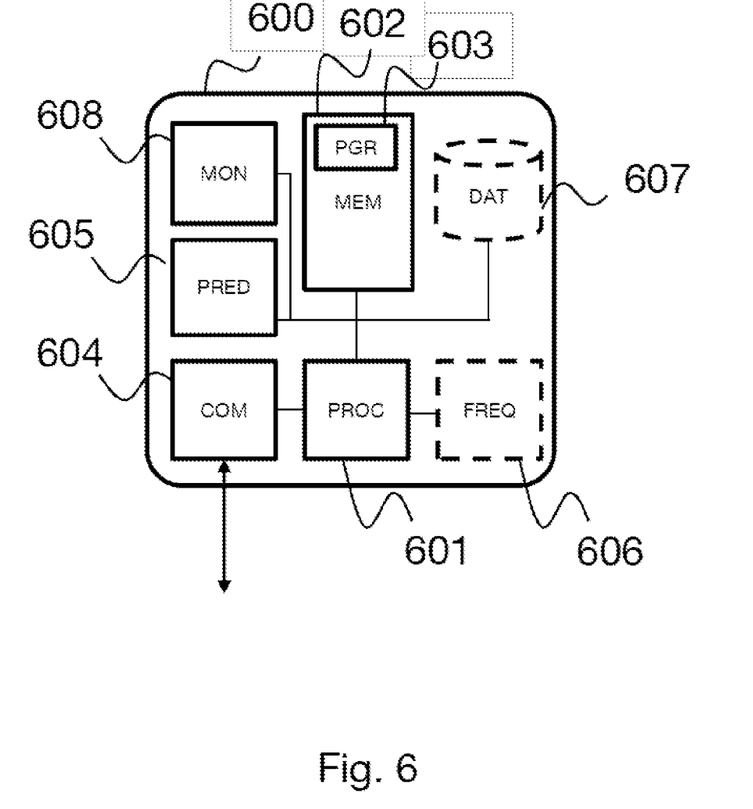
FIG. 6 illustrates a simplified architecture of a monitoring device according to a particular embodiment of the invention.

FIG. 6 illustrates a device 600 implementing the monitoring method according to a particular embodiment of the invention. The device comprises a storage space 602, for example a memory MEM, a processing unit 601 equipped for example with a processor PROC. The processing unit can be driven by a program 603, for example a computer program PGR, implementing the monitoring method as described in the invention with reference to FIG. 3, and notably the steps of reception of data from at least one sensor; of taking into account, to replace a sensor value not received, a value predicted by a prediction model representative of data previously received as long as a new datum, for which an indicator of deviation between its value and the value predicted for this datum is above a threshold, is not received; of computation of a predictive model representative of the data received over a predetermined period; and of transmission of the predictive model to at least one sensor. According to a particular embodiment, the device also implements the steps of updating of a predictive model from new data received.

On initialization, the instructions of the computer program 603 are for example loaded into a RAM memory (Random Access Memory in English) before being executed by the processor of the processing unit 601. The processor of the processing unit 601 implements the steps of the transmission method according to the instructions of the computer program 603.

For that, the device comprises, in addition to the memory 602, communication means 604 (COM) allowing the device to connect to a telecommunication network and to exchange data with other devices via the telecommunication network, and in particular to receive measurement data from a transmission device and to transmit a predictive model representative of data received. The device also comprises a computer 605 (PRED) suitable for computing a predictive model representative of the data received over a predetermined period and a monitoring module 608 (MON) suitable for taking into account, to replace a sensor value not received, a predicted value as long as a new datum for which an indicator of deviation between its value and the value predicted for this datum is above a threshold, is not received by the communication module.

According to a particular embodiment, the device comprises a module 606 for analyzing the frequency of reception of data by the communication module and a database 607 suitable for storing a set of measurement data received over an observation period.

According to a particular embodiment, the device can be incorporated in a server or a home gateway.

The invention claimed is:

1. A method for transmitting through a network, to a monitoring device, data collected by a sensor, wherein the method comprises the following acts:

acquiring a new datum by the at least one sensor for each of a plurality of time bands;

for each time band:

computing an indicator of deviation between a value of the new datum of that time band and a value predicted for this datum for the time band by a prediction model that is representative of data previously acquired, to determine whether the new datum fits the prediction model, wherein the value predicted is updated over time, determining whether the deviation indicator is above a threshold or is below the threshold;

selectively transmitting the new datum for the time band as a function of whether the deviation indicator is above or below the threshold, which comprises:

transmitting the new datum for the time band, from the sensor that acquired the new datum to the monitoring device, through the network, in response to the deviation indicator being above the threshold; or not transmitting the new datum for the time band to the monitoring device in response to the deviation indicator being below the threshold, indicating that the new datum fits the prediction model; and after transmitting at least one new datum to the monitoring device for at least one of the time bands, receiving from said monitoring device an updated prediction model computed from the transmitted at least one new datum.

2. The method as claimed in claim 1, which further comprises the following prior acts:

transmitting to the monitoring device data acquired by the at least one sensor over a predetermined time period, and receiving, from the monitoring device, the prediction model, which is representative of the data transmitted over the predetermined time period.

3. The method as claimed in claim 1, wherein the act of updating of the model is performed when a frequency of reception of new data from the sensor is above an update threshold.

4. A method for monitoring, by a monitoring server using data from a sensor, wherein the method comprises:

receiving through a network a new datum from the sensor for at least one of a plurality of time bands, wherein for at least one other of the time bands the monitoring device receives no new datum;

for each of the plurality of time bands for which a new datum is received, storing the new datum in a non-transitory computer-readable medium, wherein receipt of the new datum is indicative that deviation between a value of the new datum and a value predicted for this new datum for the time band by a prediction model is greater than a threshold, wherein the prediction model is representative of data previously acquired by the at least one sensor, wherein the value predicted is updated over time and wherein receipt of the new datum for the respective time band is indicative that the received new datum does not fit the prediction model;

for at least one of the time bands for which a new datum is not received, storing in the medium a value predicted for that time band by the prediction model, wherein lack of receipt of a new datum for the time band is indicative that data measured by the sensor for that time band fits the prediction model; and after receiving at least one new datum from the sensor for at least one of the time bands, computing an updated prediction model from the received at least one new datum to produce an updated prediction model and transmitting the updated prediction model to the sensor.

5. The method as claimed in claim 4, which further comprises the following acts by the monitoring server:

receiving the data from the sensor over a predetermined time period, computing the prediction model, which is representative of the data received over the predetermined time period, and transmitting the prediction model to the at least one sensor.

6. A transmission device for transmitting through a network, to a monitoring device, data collected by a sensor, wherein the device comprises:

a processor; and a non-transitory computer-readable medium comprising instructions stored thereon, which when executed by the processor configure the transmission device to:

an acquisition module to acquire a new datum measured by the least one sensor for each of a plurality of time bands, compute, for each time band, an indicator of deviation between a value of the new datum and a value predicted for this new datum for the time band by a prediction model that is representative of data previously acquired, to determine whether the new datum fits the prediction model, wherein the value predicted is updated over time, compare the deviation indicator to a threshold and determine whether the deviation indicator is above the threshold or is below the threshold, and selectively transmit the new datum for the time band as a function of whether the deviation indicator is above or below the threshold, by:

transmitting the new datum for the time band through the network to the monitoring device in response to the deviation indicator being above the threshold; or not transmitting the new datum for the time band to the monitoring device in response to the deviation indicator being below the threshold, indicating that the new datum fits the prediction model, and after transmitting at least one new datum to the monitoring device for at least one of the time bands, receiving from said monitoring device an updated prediction model computed from the transmitted at least one new datum.

7. A terminal, which comprises a transmission device as claimed in claim 6.

8. A monitoring device comprising:

a processor; and at least one non-transitory computer-readable medium comprising instructions stored thereon, which when executed by the processor configure the transmission device to:

receive through a network a new datum from a sensor of a monitoring system for at least one of a plurality of time bands, for each of the plurality of time bands for which a new datum is received, store new datum the data in the at least one non-transitory computer-readable medium, wherein receipt of the new datum is indicative that deviation between a value of the new datum and a value predicted for this new datum for the time band by a prediction model is greater than a threshold, wherein the prediction model is representative of data previously acquired by the at least one sensor, wherein the value predicted is updated over time and wherein receipt of the new datum for the respective time band is indicative that the received new datum does not fit the prediction model, for at least one of the time bands for which a new datum is not received, read a value predicted by the prediction module for that time band and store in the medium the value predicted, wherein lack of receipt of a new datum for the time band is indicative that data measured by the sensor for that time band fits the prediction model, and after receiving at least one new datum from the sensor for at least one of the time bands, compute an updated prediction model from the received at least one new datum to produce an updated prediction model and transmit the updated prediction model to the sensor.

9. The monitoring device as claimed in claim 8, wherein the instructions further configure the monitoring device to receive the data from the sensor over a predetermined time period, compute the prediction model, which is representative of the data received over the predetermined time period, and transmit the prediction model to the at least one sensor.

10. A server, which comprises a monitoring device as claimed in claim 8.

* * * * *

UNITED STATES PATENT AND TRADEMARK OFFICE
CERTIFICATE OF CORRECTION

PATENT NO. : 10,841,125 B2
APPLICATION NO. : 15/537649
DATED : November 17, 2020
INVENTOR(S) : David Cibaud et al.

Page 1 of 1

It is certified that error appears in the above-identified patent and that said Letters Patent is hereby corrected as shown below:

In the Claims

In Claim 1, Column 11, Line 5:
Please delete "at least one".

In Claim 6, Column 12, Line 24:
Please delete "an acquisition module to".

In Claim 6, Column 12, Line 25:
Please delete "least one".

Signed and Sealed this
Twenty-second Day of February, 2022

Drew Hirshfeld
*Performing the Functions and Duties of the*
*Under Secretary of Commerce for Intellectual Property and*
*Director of the United States Patent and Trademark Office*